United States Patent [19]
Butterworth et al.

[11] 3,967,623
[45] July 6, 1976

[54] DISPOSABLE ABSORBENT PAD

[75] Inventors: George A. M. Butterworth, Western Springs; Robert T. Elias, Downers Grove, both of Ill.

[73] Assignee: Johnson & Johnson, New Brunswick, N.J.

[22] Filed: June 30, 1975

[21] Appl. No.: 591,747

[52] U.S. Cl. .............................. 128/287; 128/156; 128/284
[51] Int. Cl.² .................... A41B 13/02; A61F 13/16
[58] Field of Search .................. 128/156, 284, 287; 264/56, 72, 88

[56] References Cited
UNITED STATES PATENTS

| 3,292,619 | 12/1966 | Egler | 128/156 |
| 3,344,789 | 10/1967 | Arnold et al. | 128/287 |
| 3,399,672 | 9/1968 | Crowe, Jr. et al. | 128/256 |
| 3,814,101 | 6/1974 | Kozak | 128/287 |
| 3,886,941 | 6/1975 | Duane | 128/287 |
| 3,916,447 | 11/1975 | Thompson | 128/287 |

Primary Examiner—Aldrich F. Medbery

[57] ABSTRACT

A disposable absorbent pad such as a diaper, sanitary napkin, underpad, surgical dressing or wipe, and the like, is made from a flexible, body fluid-impermeable backing sheet, a layer of absorbent material on the backing sheet, and a soft, body fluid-permeable facing sheet which overlies the absorbent material. The facing sheet is a perforate, substantially hydrophobic thermoplastic web having an integral fibrous or sueded outer surface. In addition to being useful as a separate entity the absorbent pad of this invention can also be incorporated into a disposable or limited use garment as an integral part thereof.

12 Claims, 4 Drawing Figures

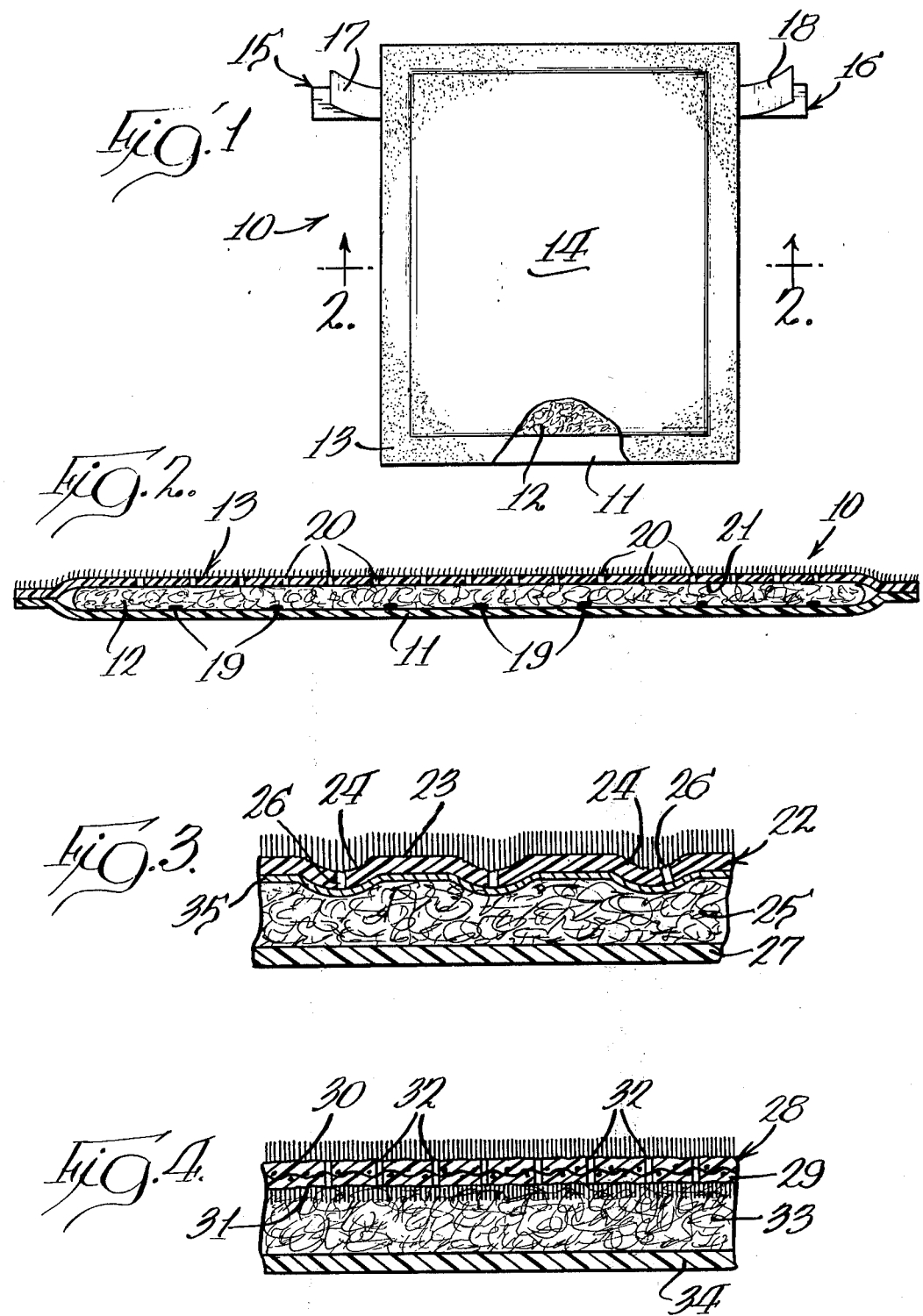

DISPOSABLE ABSORBENT PAD

BACKGROUND OF THE INVENTION

This invention relates to disposable absorbent pads such as diapers, sanitary napkins, underpads, surgical dressings and wipes, and the like.

Non-woven, bonded, textile/pulp fabrics, hydraulically-entangled and mechanically-bonded textile fiber fabrics, and relatively thin, spun-bonded fabrics are the usual facing fabrics for disposable sanitary and convenience products. Such fabrics should be relatively soft and conformable, capable of extended contact with external and internal body surfaces without causing chafing or allergenic reactions, and also capable of transmitting body fluids to a central absorbent core or layer while maintaining skin dryness. However, such facing fabrics are relatively expensive inasmuch as synthetic polymeric materials must be first converted to textile filaments or fibers, and the synthetic or natural textile length fibers must be further converted into a web structure and mechanically, hydraulically, or adhesively bonded to produce a facing fabric which meets the aforementioned requirements.

In order to minimize the cost of disposable sanitary and convenience products it is desirable to develop disposable absorbent pads which do not utilize a fabric-type facing sheet yet which retain the above comfort and conformability characteristics.

U.S. Pat. No. 3,431,911 to Meisel discloses an absorbent pad having a facing layer made of open-cell polymeric foam which is disposed over an underlying layer of fluid absorbent material. However, foamed facing layers are relatively bulky and tend to increase the overall dimensions of the absorbent pad. Moreover, the open-cell structure of the foam layer may cause undesirable reverse pumping action when an absorbent pad of such type is compressed while being used. In addition, foam surfaces do not have the desired surface aesthetics.

U.S. Pat. No. 3,665,921 to Stumpf discloses a disposable diaper having a liner made of a discontinuous sheet material bearing a plurality of individually-looped, textile length hydrophobic fibers embedded in the sheet material. However, such liners are relatively expensive to manufacture and are not commercially attractive as components of disposable items.

SUMMARY OF THE INVENTION

The present invention contemplates an absorbent pad which does not utilize a facing fabric yet which retains the desirable characteristics of a fabric facing material but at a reduced cost. The absorbent pad comprises a flexible backing sheet impermeable to body fluids, a layer of absorbent material on the backing sheet, and a soft, body-fluid permeable facing sheet which overlies the absorbent material. The facing sheet is a perforate, substantially thermoplastic web having an integral fibrous or sueded outer surface made up of elementary fibers, i.e., fibers having a mean length-to-diameter ratio of less than 1000. A surface active agent, such as the sodium salt of dioctyl sulfosuccinate, can be deposited on or incorporated into the thermoplastic web to control surface wettability and to promote liquid transport through the facing sheet. The absorbent pads of this invention are useful for absorbing body fluids. The absorbent pads can be used as separate entities or as an integral part of a disposable or a limited use garment.

BRIEF DESCRIPTION OF THE DRAWING

In the drawing,
FIG. 1 is a plan view showing a disposable diaper embodying the present invention;
FIG. 2 is a sectional elevation on an enlarged scale taken along plane 2—2 in FIG. 1;
FIG. 3 is a fragmentary sectional elevation on an enlarged scale illustrating a further embodiment of this invention; and
FIG. 4 is a fragmentary sectional elevation on an enlarged scale illustrating yet another embodiment of the present invention.

DESCRIPTION OF PREFERRED EMBODIMENTS

As illustrated in FIGS. 1 and 2, an absorbent pad of this invention such as disposable diaper 10 comprises flexible backing sheet 11, absorbent panel 12 which is a layer of fluffy absorbent material positioned on backing sheet 11, and facing sheet 13 which is a thermoplastic web having fibrous outer surface 14. During use, surface 14 is in contact with the user of the absorbent pad. Diaper 10 is also equipped with fastening tabs 15 and 16 which comprise a pressure-sensitive adhesive layer on a flexible backing or substrate. The adhesive layer on each tab is protected prior to use by removable cover strips 17 and 18 which are segments of paper or similar web-like material bearing a suitable release compound on the side thereof in contact with the adhesive layer.

Facing sheet 13 and backing sheet 11 usually are substantially coextensive and are joined together about the periphery of pad 10 by thermal fusion, adhesive, or in any other convenient manner. If desired, absorbent layer or panel 12 can be anchored to backing sheet 11 by one or more glue lines 19. A suitable backing sheet material can be an opaque polyethylene web impermeable to body fluids and about 0.001 inch thick. Another suitable sheet material for this purpose is a polyethylene terephthalate web having a thickness of about 0.0005 inch.

Absorbent panel 12 can be a fluffy batt cut from a relatively loose web of non-woven fibers having a relatively high absorptive capacity. Panel 12 usually is of a rectangular configuration and somewhat smaller than backing sheet 11. Particularly suitable absorbent layers or panels can be made in accordance with the teachings of U.S. Pat. No. 3,612,055 to Mesek et al.

Absorbent panel 12 can also be a fibrous batt having an integral densified layer positioned on the backing sheet of the pad so that the densified layer adjoins the backing sheet. The densified layer has relatively higher wettability and liquid retentivity than the rest of the aforesaid batt and usually is formed by slightly moistening one surface of the batt and thereafter compressing the moistened surface. The nature of the batt having an integral densified layer as well as the method of producing same are described in detail in U.S. Pat. No. 3,017,304 to Burgeni.

Facing sheet 13 is a substantially hydrophobic thermoplastic web provided with random or evenly-spaced perforations or pores 20 sufficient in number to permit a ready transport of excreted body fluids or exudates to absorbent layer 12. Additionally, facing sheet 13 is provided with soft, fibrous outer surface 14 which comprises elementary fibers or tufts integral with and carried by the thermoplastic web. These fibers are much shorter than textile-length fibers and have a mean length-to-diameter ratio of less than 1000; usually the length of these elementary fibers is about ¼ inch, or less. In this manner, a comfortable outer covering of high liquid throughput capability and having a good, warm feel or hand is provided in contact with the wearer. At the same time fibrous outer surface 14 provides an effective barrier which prevents the protrusion of undesirable fiber ends from the underlying abosrbent panel 12 through perforations 20 and obviates a potential source of discomfort to the wearer. Also, fibrous outer surface 14 permits air circulation adjacent to the wearer's skin and minimizes the possibility of skin degradation due to excessive moisture.

Hydrophobicity is desirable for facing sheet 13 in order to enhance comfort of the wearer by having a substantially dry contact surface between the wearer and the absorbent pad, yet from the standpoint of liquid transport through facing sheet 13, preferably at least portions thereof initially should be hydrophilic in character so as to initiate liquid flow to absorbent layer 12, especially when perforations or pores 20 in facing sheet 13 are relatively small. To this end facing sheet 13 can be treated with a surface active agent or mixtures thereof, for example, with the sodium salt of dioctyl sulfosuccinate (commercially available under the designation Aerosol OT), nonionic polyoxyethylene sorbitan monolaurate (commercially available under the designation Tween 20), or the like, by spraying an aqueous solution of the desired surface active agent onto fibrous outer surface 14 and subsequent drying. The surface active agent can also be deposited on facing sheet 13 by means of a roller wet with an aqueous solution of the surface active agent which is passed over inner surface 21 of facing sheet 13 so as to deposit the surface active agent in perforations 20 and on inner surface 21 while fibrous outer surface 14 retains its substantially hydrophobic character. In the alternative, internal surfactants or wetting agents can be incorporated into the thermoplastic web during manufacture. Suitable wetting agents for this purpose can be nonionic surfactants based on ethylene oxide, fatty alcohol ethers, ethoxylated adducts of propylene oxide with propylene glycol, fatty esters or sorbitol and glycerol, and the like.

Thermoplastic facing sheets having a fibrous outer surface can be produced by applying a thickness of a molten thermoplastic polymer to a carrier web by a doctor blade arrangement and thereafter passing the carrier web bearing the layer of molten or softened polymeric mass under a heated roller which fibrillates the exposed surface of the molten polymer layer by pulling or ripping polymeric filaments therefrom. An air jet or a similar cooling gas stream is then impinged onto the resulting fibrillated surface to cool the polymeric mass below its softening temperature so as to produce an integral pile surface. The carrier web can be absorbent paper tissue which can be advantageously utilized for liquid transport into the absorbent pad as will be discussed in greater detail hereinbelow.

Thereafter the produced thermoplastic web with a fibrous surface is slit, punctured, buffed, stretch-fractured, or otherwise mechanically worked to produce a perforate web. Porosity of the thermoplastic web can also be produced by incorporating into the polymeric mass prior to web formation soluble particulate materials which are subsequently leached out, or by striking a plurality of random electric arcs therethrough.

Suitable thermoplastic polymers that can be utilized to produce perforate webs having at least one fibrous surface are polyethylene, polypropylene, polyvinyl chloride, polycaprolactam, polyamide, polyurethane, polyethylene terephthalate, mixtures of polyvinyl chloride and butadiene-acrylonitrile elastomers, and the like. The webs produced for use as facing sheets in accordance with the present invention usually are about 2 to about 20 mils thick.

Several other methods can also be utilized to produce a web having an integral fibrous or fiber-like surface. For instance, a precast thermoplastic film can also be passed over a smooth roller maintained at a temperature sufficiently high to melt the surface layer of the film in contact therewith which molten surface layer is subsequently ripped from the roller so as to fibrillate the surface layer as described hereinabove.

The foregoing methods of producing a thermoplastic web with a fibrous surface are disclosed in U.S. Pat. No. 3,708,565 and British Pat. No. 1,139,165. Moreover, a scrim or the like can be coated with a molten polymer to provide a self-supporting web which is subsequently fibrillated as described above on one or both sides of the web to provide a fibrous surface and then perforated. Fibrous surfaces on one or both sides of the facing sheet permit the use of relatively large slits in the facing layer while providing an effective retaining screen even for relatively short fibers or linters present in the absorbent layer, thereby preventing dusting. Such a retaining screen is particularly desirable when particulate superabsorbent materials such as the so-called hydrocolloids or hydrogels are also present distributed within the absorbent layer. Additionally, a fibrous inner surface of the facing layer provides a convenient means for increasing the total surface treated with a surface active agent within the pad while maintaining the outer facing sheet surface relatively hydrophobic.

Still other methods that can be used to prepare a thermoplastic web having an integral fibrous surface include pressure molding or embossing of a desired surface texture onto the thermoplastic surface, treating or brushing the surface of a relatively smooth thermoplastic web to roughen the web surface and to produce a soft, cushiony appearance and feel, coating the surface of a smooth thermoplastic web with fibrous polymeric particles of elementary fiber size while the surface of the thermoplastic web is in a molten or tacky state. Spray, melt blowing, electrical or tack spinning, candy floss techniques, and the like can be utilized for this purpose. Such methods are known in the art and are described, for example, in U.S. Pat. No. 3,098,262; U.S. Pat. No. 3,141,051; U.S. Pat. No. 3,316,592; U.S. Pat. No. 3,655,497; U.S. Pat. No. 3,696,183; and U.S. Pat. No. 3,701,621.

Another embodiment of this invention is illustrated in FIG. 3. Polyethylene facing sheet 22 having integral fibrous outer surface 23 overlies absorbent layer 25 and is provided with a plurality of valvular indentations 24 in which excreted body fluid collects prior to being absorbed within absorbent layer 25 of the produced pad. Each valvular indentation is provided with at least one slit 26 which communicates with underlying absorbent layer 25. A thin web of absorbent tissue such as web 35 integral with facing sheet 22, and initially serving as a carrier web for the molten polymeric mass during the aforedescribed surface fibrillation treatment, functions as a wicking sheet for the excreted body fluids and assists in the distribution thereof over the lateral surface of absorbent layer 25 after facing sheet 22 is slit or otherwise perforated. Wicking sheet 35 can be impregnated with a surface active agent, if desired; however, in many instances it is not necessary to do so. Polyethylene backing sheet 27 retains absorbed liquids within the pad and is fused to perforate facing sheet 22 about the periphery of the pad.

A still further embodiment of this invention is shown in FIG. 4. Perforate thermoplastic facing sheet 28 is reinforced by scrim 29 and is provided with fibrous outer surface 30 as well as fibrous inner surface 31. Perforations 32 in facing sheet 28 communicate with underlying fibrous absorbent batt 33 which rests on backing sheet 34. A surface active agent, e.g., the sodium salt of dioctyl sulfosuccinate, is deposited as a spray on the fibers of inner surface 31 and promotes liquid transport from outer surface 30 to absorbent batt 33. The individual fibers of inner surface 31 intermingle with the individual fibers of batt 33 and provide a plurality of liquid flow paths into batt 33 as well as assist in minimizing a lateral shift of batt 33 relative to facing sheet 28.

The absorbent pads of the present invention can be of various shapes and configurations depending on the intended end use, e.g., as disposable diapers, sanitary napkins, underpads, surgical dressings or wipes, and the like. Additionally, the present absorbent pads can be incorporated into a disposable or limited use garment as an integral part thereof. For example, an absorbent pad can be a part of disposable training pants and similar garments.

The foregoing description and the drawing are intended as illustrative and are not to be taken as limiting. Still other variations are possible without departure from the spirit and scope of this invention.

What is claimed is:

1. An absorbent pad comprising a flexible, body fluid-impermeable backing sheet, a layer of absorbent material on said backing sheet, and a soft, body fluid-permeable facing sheet overlying said absorbent material; said facing sheet being a perforate, substantially hydrophobic thermoplastic web having an integral fibrous outer surface made up of elementary fibers carried by said web.

2. The absorbent pad in accordance with claim 1 wherein the fibrous outer surface is a pile surface.

3. The absorbent pad in accordance with claim 1 wherein a surface active agent is present on said thermoplastic web.

4. The absorbent pad in accordance with claim 3 wherein the surface active agent is present on said fibrous outer surface.

5. The absorbent pad in accordance with claim 3 wherein the surface active agent is present on the inner surface of said thermoplastic web.

6. The absorbent pad in accordance with claim 1 wherein a carrier scrim is embedded in said thermoplastic web and a fibrous inner surface is also provided on said thermoplastic web.

7. The absorbent pad in accordance with claim 6 wherein a surface active agent is present on said fibrous inner surface.

8. The absorbent pad in accordance with claim 1 wherein said thermoplastic web is provided with a plurality of valvular indentations and each of the indentations is provided with at least one elongated slit.

9. The absorbent pad in accordance with claim 8 wherein surface active agent is present in said valvular indentations.

10. The absorbent pad in accordance with claim 1 wherein a wicking sheet is provided between said perforate thermoplastic web and said layer of absorbent material.

11. The absorbent pad in accordance with claim 1 wherein a surface active agent is incorporated into said thermoplastic web.

12. A disposable garment including, as an integral part thereof, an absorbent pad comprising a flexible, body fluid-impermeable backing sheet, a layer of absorbent material on said backing sheet, and a soft, body-fluid permeable facing sheet overlying said absorbent material; said facing sheet being a perforate, substantially hydrophobic thermoplastic web having an integral fibrous outer surface made up of elementary fibers carried by said web.

* * * * *